(12) United States Patent
Roteliuk et al.

(10) Patent No.: US 6,371,923 B1
(45) Date of Patent: Apr. 16, 2002

(54) TIME-DOMAIN SYSTEM AND METHOD FOR RELAXATION MEASUREMENT AND ESTIMATION OF INDICATOR DILUTION FOR CONTINUOUS ESTIMATION AND DISPLAY OF CARDIAC EJECTION FRACTION AND END DIASTOLIC VOLUME

(75) Inventors: Luchy D. Roteliuk, Lake Forest, CA (US); Russell McKown, Richardson, TX (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 09/456,049

(22) Filed: Dec. 7, 1999

(51) Int. Cl.$^7$ .......................... A61B 5/026; A61B 5/028
(52) U.S. Cl. ......................................... 600/526
(58) Field of Search .......................... 600/526

(56) References Cited

U.S. PATENT DOCUMENTS 5,357,967 A * 10/1994 Dixon et al. ............... 600/526
5,687,733 A * 11/1997 McKown .................... 600/505
6,045,512 A *  4/2000 Roteliuk et al. ............ 600/505

OTHER PUBLICATIONS

M. Yelderman: "Continuous Measurement of Cardiac Output with the Use of Stochastic System Identification Techniques" Journal of Clinical Monitoring, vol. 6 No. 4, Oct. 1990, pp. 322–332, Bostpn, MA.

* cited by examiner

*Primary Examiner*—Carl Layno
(74) *Attorney, Agent, or Firm*—Jeffrey Slusher, Esq.; Lena I. Vinitskaya, Esq.

(57) ABSTRACT

The invention estimates a cardiac performance value such as cardiac output (CO) and cardiac ejection fraction (EF) by sensing a downstream indicator concentration signal y(t) that corresponds to an indicator (preferably heat) signal x(t) injected upstream in a patient's blood channel. The signal x(t) is preferably generated as a series of alternating transitions between a high state and a low state, such as a PRBS signal. The signal y(t) is then divided into at least one sub-signal that is synchronous with x(t). A decay parameter τ that minimizes a cost function that includes a time-domain channel relaxation model is then calculated. The cardiac performance value is then calculated based on this value for τ. For each transition of the injected indicator signal, a corresponding segment of the indicator concentration signal is preferably isolated, and a segment relaxation parameter is then calculated. The decay parameter τ is then estimated as a predetermined function of the segment relaxation parameters. In embodiments of the invention in which x(t) is periodic, the invention also generates estimates of τ by finding the minimum of a cost function between a model of the channel and an average of several cycles of y(t), each corresponding to one period of x(t).

37 Claims, 4 Drawing Sheets

FIG 2A
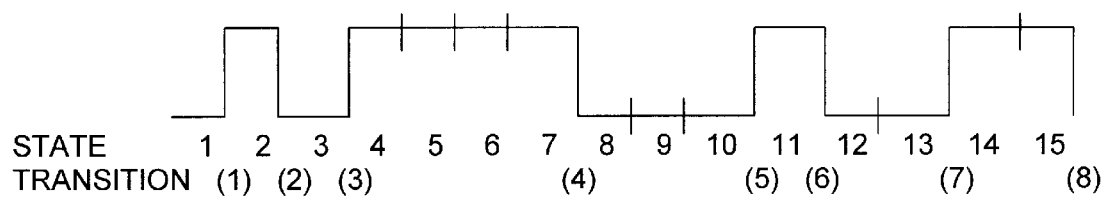
STATE            1   2   3   4   5   6   7   8   9   10  11  12  13  14  15
TRANSITION     (1) (2) (3)             (4)         (5) (6)     (7)     (8)
FIG 2B
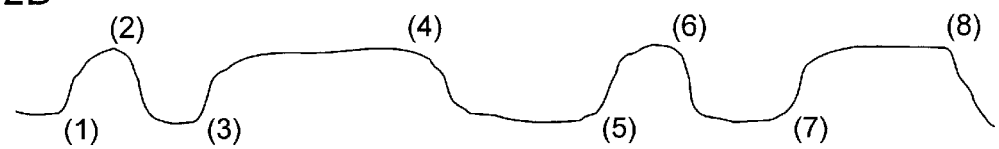
FIG. 2C
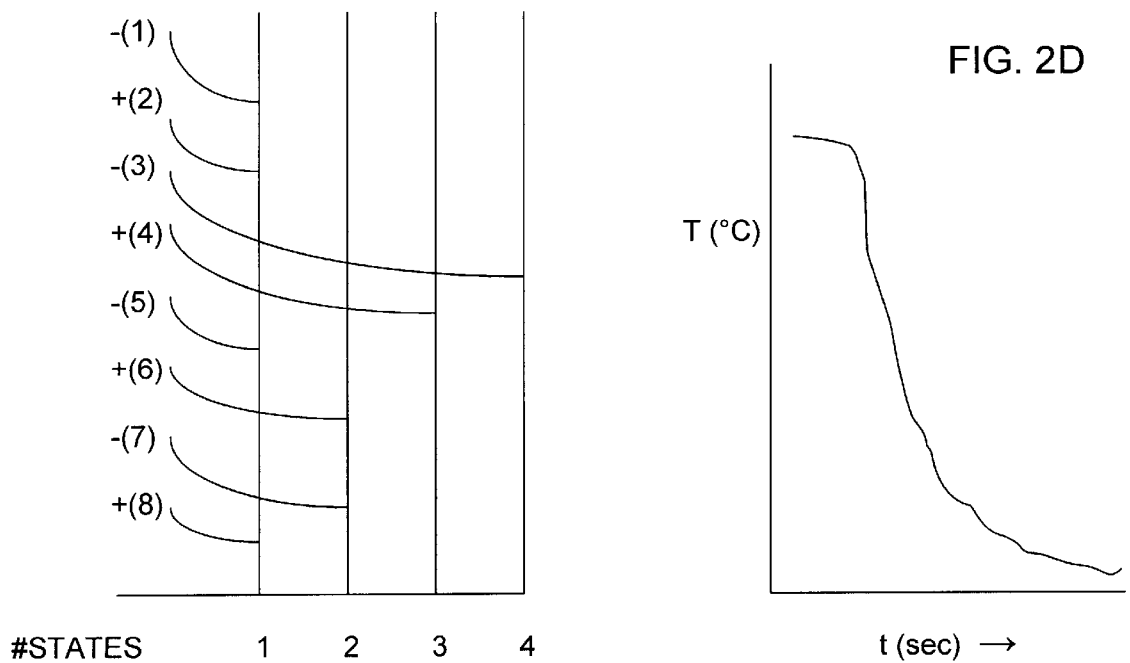
FIG. 2D

TIME-DOMAIN SYSTEM AND METHOD FOR RELAXATION MEASUREMENT AND ESTIMATION OF INDICATOR DILUTION FOR CONTINUOUS ESTIMATION AND DISPLAY OF CARDIAC EJECTION FRACTION AND END DIASTOLIC VOLUME

BACKGROUND OF THE INVENTION

1. Field of the Invention

This invention relates to the in-vivo determination and display of estimates of the cardiac ejection fraction, or the end diastolic volume, or both.

2. Description of the Related Art

Information about the output of a patient's heart is very valuable to a surgical team operating on the patient or to physicians who are trying to diagnose an illness or monitor the patient's condition. Few hospitals are therefore without some form of conventional equipment to monitor cardiac output.

One common way to determine cardiac output is to mount some flow-measuring devices on a catheter, and then to thread the catheter into the patient and to maneuver it so that the devices are in or near the patient's heart. Some such devices inject either a bolus or heat at an upstream position, such as in the right atrium, and determine flow based on the characteristics of the injected material or energy at a downstream position, such as in the pulmonary artery.

For example, U.S. Pat. No. 4,236,527 (Newbower et al., Dec. 2, 1980) and U.S. Pat. No. 4,507,974 (Yelderman, Apr. 2, 1985), describe systems for measuring cardiac output in which heat is used as an indicator. In such heat-based systems, a balloon catheter is typically positioned proximal to the branch of the pulmonary artery via the right atrium and the right ventricle. The catheter includes a resistive heating element, which is positioned in the atrium and/or ventricle, and a thermistor, which is positioned in the artery. Cardiac output is then calculated as a function of the sensed downstream temperature profile.

U.S. Pat. No. 5,146,414 (McKown, et al., Sep. 8, 1992) describes a system in which the transfer function of the channel (the region from where an indicator such as heat is applied to the blood upstream to the downstream position where the indicator concentration, such as temperature, is sensed) is modeled, the approximate spectrum of the noise is determined, and the output of the system is used in a feedback loop to adaptively update the parameters of the model and thus to improve the estimate of cardiac output (CO). U.S. Pat. No. 5,687,733 (McKown, et al., Nov. 18, 1997) describes an improvement over the earlier McKown '414 system that estimates both the CO trend and an instantaneous CO value. Moreover, in the McKown systems, only the zero-frequency (dc or steady state) gain of the channel is required to get an estimate of the cardiac output (CO).

Although these known systems provide estimates of cardiac output with varying degrees of accuracy, they fail to provide any estimate of the heart's ejection fraction (EF), typically, the right ejection fraction (REF), which is defined as the ratio between the stroke volume (SV) of the heart and its end diastolic volume (EDV). The ejection fraction is thus a measure of how efficiently the heart pumps out the blood that it can contain.

Because of its diagnostic importance, there are several known methods for measuring EF. Such systems, however, frequently rely on the use of an injected bolus and on evaluation of the washout (thermodilution) curve in the blood vessel. U.S. Pat. No. 4,858,618 (Konno, et al., issued Aug. 22, 1989), for example, describes a thermodilution system for determining right ventricular ejection fraction. In this known system, a cold bolus indicator is injected into the right ventricle. Pre- and post-bolus temperatures are sensed in the pulmonary artery. The temperature differentials are used to determine the ejection fraction.

One problem with using a bolus to determine EF is that it is difficult to establish just where on the sensed bolus curve the measurements are to begin, since the front side of the curve depends heavily on mixing, on the heart rate, and even on how fast the administering nurse is pushing the syringe plunger while injecting the bolus. Another problem faced by all such known systems is that they require synchronization with the heart cycle in order to reduce the effects of the heartbeat when producing an EF estimate. Some systems synchronize based on plateaus in the washout curve, but this presupposes a fast and very accurate thermistor. Other systems rely for synchronization on an EKG trigger. EKG synchronization, however, is difficult, since it is then necessary to slave in and precisely coordinate the timing of other instruments, each gathering its own data.

Further problems of existing systems for determining EF stem from their need to identify discrete plateaus in the dilution profiles created by the heart beats. This is necessary because these systems use the plateaus as markers in order to fit exponential or ratio-based curves to the data, which are in turn used to evaluate the dilution decay. This approach is accurate in practice, however, only for a relatively slow heart rate and a thermistor whose response is significantly faster than the decay parameter $\tau$.

In effect, these conventional systems assume a square-wave dilution curve. This is, however, usually an unrealistic assumption. First, most of the patients needing EF measurements in a hospital are not in the best of health; rather, they tend to have relatively high and erratic heart rates. Furthermore, in systems that use a bolus of relatively cold fluid, the sensed heart rate is likely to be incorrect since the cold bolus itself tends to affect not only the heart rate, but also its regularity. Second, real thermistors distort the plateaus, so that the exponential fits themselves become distorted. Third, as the EF rises, the drops in the plateaus also rise. This causes the systems to use fewer plateaus, and thus reduce their accuracy, because of the limited signal-to-noise ratios of these systems.

For example, one known system uses a fast response injectate cardiac output pulmonary artery catheter together with an electrocardiogram R-wave detector to measure EF and EDV. The exponential method of measuring REF then synchronizes R-wave events with plateaus occurring during the downslope of a thermodilution curve and fits the decay of the curve with an exponential function. Thus, if T(i) is the PA temperature after the i-th R-wave and T(i−n) is the temperature n R-waves earlier in time, then:

$$T(i)=T(i-n)*\exp(-t/\tau), \qquad \text{(Equation 1)}$$

where t is time and $\tau$ is the decay parameter.

The physiological washout decay can then be represented by $(1-EF)^n$, where n is the number of R-waves in the observation interval (for example, from 80% down to 30% of the peak). One can then represent time in terms of the heart rate (HR):

$$t=n*60/HR \qquad \text{(Equation 2)}$$

where HR is the local average from the (i−n)'th to the i'th R-wave in beats per minute. Given these relationships, the following can then be shown:

$$EF=1-\exp(-60/(\tau*HR)). \qquad \text{(Equation 3)}$$

One of the problems with this system is that the thermistor must have a sufficiently fast response time to allow measurement of the true physiological decay time. At low heart rates, this puts plateaus in the temperature data during systole, which must be dealt with in determining the decay parameter T. This is, indeed, the primary reason for the R-wave synchronization, since, other than that, the local average HR is all that is required.

Another problem with this known system is that it is bolus-based and intermittent by nature. In addition, only part of the temperature data is used (from the R-wave around 80% washout to the R-wave around 30% washout: typically one-five R-waves). This introduces variability or lack of precision into the measurement of the injectate cardiac output (ICO) due to irregular R-wave intervals or large noise sources such as respiratory ventilation.

The earlier McKown systems improve on such a bolus-based approach by instead generating an input injectate signal, preferably in the form of a pseudo-random binary heat signal, and then estimating the parameters of a transfer function model of the input-output channel. The preferred model used is the lagged normal transfer function (described below). Both the measurement and the modeling of the transfer function model are carried out in the frequency domain at the harmonics of the preferred input injectate signal. In order to understand the weaknesses of these systems, it is helpful to have at least a basic understanding of the lagged normal model of the transfer function.

In the context of estimating cardiac output, the "lagged normal model" described by Bassingthwaighte, et al. in "Application of Lagged Normal Density Curve as a Model for Arterial Dilution Curves," Circulation Research, vol. 18, 1966, has proven to be particularly accurate and useful, and it is therefore the model for cardiac output used in, for example, McKown '733. The lagged normal model is defined as a linear, time-invariant system (LTIS) whose impulse response is the convolution of a unity-area Gaussian (normal distribution) function and a unity-area decaying exponential. The Gaussian has two parameters: the mean $\mu$ and the standard deviation $\sigma$. The exponential has one parameter: the time-decay parameter $\tau$. The unity-gain, lagged-normal transfer function $H_{\_LN}$ at each frequency $\omega$ sampled ($\omega$ is the independent variable in this model) thus depends on $\mu$, $\sigma$, and $\tau$ as follows:

$$H_{\_LN}(\omega|\mu,\sigma,\tau)=\exp[-j\cdot\omega\cdot\mu-(\omega\cdot\sigma)^2/2]/(1+j\cdot\omega\cdot\tau) \quad \text{(Equation 4)}$$

where exp is the exponential function and the physical meaning of the parameters is:

$\mu$: a pure time delay that represents translational flow $\sigma$: a measure of random dispersion $\tau$: the decay parameter, that is, a time constant associated with mixing in a distribution volume, which, in this example, is the blood vessel.

The units of $\mu$, $\sigma$, and $\tau$ are time (seconds) and the units of $\omega$ are radians per second.

This model is used in, for example, not only in the McKown '733 system, but also in a more recent system described in the U.S. patent application Ser. No. 09/094,390, FILED ON Jun. 9, 1998 by the same inventors as those of the present invention, which build on the McKown '733 techniques.

Although other indicators may be used, in the preferred embodiment of these systems, heat is used as the indicator, and the indicator driver signal is a pseudo-random binary sequence (PRBS). The driver/sensor pair therefore preferably consists of a heater and a thermistor. $H_{\_LN}$ is then estimated as an optimized fitting of a vector of complex values Hxy($\omega_n$), each representing a measurement of the transfer function between a heater power signal x and a thermistor temperature signal y. Each vector contains the parameters fitted to the measured temperature data at each of ten frequencies $\omega_n$ (the first ten PRBS harmonics).

More specifically, the system in McKown '733 computes the state vector X=[dc, $\mu$, $\sigma$, $\tau$] that minimizes the cost function Cost_Hxy, defined as:

$$\text{Cost\_Hxy} = \text{SUM}[\text{Hxy}_{\_SAE}(\omega_n|X)\cdot W(\omega_N)] \quad \text{(Equation 5)}$$

where the sum is taken over N=1 to 10 (or however many harmonics are used), W($\omega_n$) are weights and:

$$\text{Hxy}_{\_SAE}(\omega_n|X)=[\text{Hxy\_avg}(\omega_n)-\text{dc}\cdot\text{Hxy}_{\_LN}(\omega_N|X)]^2 \quad \text{(Equation 6)}$$

which is the squared absolute error (SAE) of the averaged measured transfer function Hxy_avg($\omega_n$) relative to the lagged normal transfer function model Hxy$_{\_LN}$($\omega_n$|X) at the PRBS harmonic frequencies $\omega_n$ given the state vector X=[dc, $\mu$, $\sigma$, $\tau$].

Once $\mu$, $\sigma$, and $\tau$ are known, then each of the ten complex measured numbers Hxy($\omega_N$) would individually provide an estimate of cardiac output (CO) according to:

$$\text{CO}(n)=K\cdot H_{\_LN}(\omega_n)/\text{Hxy}(\omega_n) \text{ for n=1 to 10} \quad \text{(Equation 7)}$$

where K is a known or experimentally determinable conversion constant.

In order to apply this relationship, the McKown '733 system first determines not only what the values of $\mu$, $\sigma$, and $\tau$ should be, but also how the ten cardiac output estimates CO(n) should be combined. One should note that the cardiac output does not depend on the shape of H($\omega$), or Hxy($\omega$), but only on the zero-frequency gain, dc, of Hxy. Since the experimental transfer function Hxy is measured at ten frequencies $\omega_n$ that are not zero, however, the McKown '733 system in essence extrapolates the measured Hxy($\omega$) to zero frequency. A known optimization routine is then used to provide a best fit of the ten modeled transfer function values H_xy to the observed values. The relationship shown above for CO can then be reduced to CO=K/dc, where dc is the zero-frequency ($\omega$=0) gain value in units of degrees Celsius per watt, and K is an experimentally determined constant with the unit (liters per minute)/(degrees Celsius per watt).

Note that the McKown '733 system provides a continuous CO value (equivalently, the dc value), as well as the decay parameter $\tau$. Note that "continuous" does not here mean that displayed values are "continuously changing," but rather that they can be updated every processing cycle (preferably a PRBS cycle), after an initialization period.

There are, however, problems with the prior-art technologies, which are based on frequency domain (typically, cross-correlation) transfer function measurement and modeling. A primary limitation of these prior-art techniques is that stated by W. D. Davies in "System Identification for Self-Adaptive Control," Wiley-Interscience, 1970, namely, that "since the technique described here may also be considered as one of identifying the frequency response of an unknown system, it will also unfortunately combine in the final estimate the frequency components of the noise that lie within the system bandwidth, and to date there exists no theory that allows the separation of the signal from the noise."

In the McKown '414 and '733 systems, for example, only the transfer function's dc-gain is used, whereas, in other systems, such as in the U.S. patent application Ser. No. 09/094,390, the indicator decay time-constant $\tau$ is used, in addition to a heart rate estimate. A problem of these prior art approaches is, however, the degree to which estimation errors are coupled between the parameters dc, τ, σ, and μ. This coupling is primarily due to the low-frequency thermal (indicator) noise, for example, the noise created by the patient's respiration, whether natural or mechanically ventilated. The parameter estimation then adversely affects the estimate of the cardiac output, and also often degrades the accuracy of the estimated REF and EDV so badly that the measurements become clinically unacceptable.

Another problem of these earlier techniques is their use of the four-parameter (dc, μ, σ, τ) lagged normal frequency domain model to analyze the transfer function data. Typically, if enough noise is present, then the optimization routine (for example, squared error cost function minimization) may converge to local or false minima for the vector (μ, σ, τ) of shape parameters. In other words, there may be several "best" combinations of μ, σ, and τ, most or even all of which are bad in the sense of lying too far from the true values. Although this affects the quality of continuous cardiac output (CCO) measurements only slightly (due to some dc–τ coupling) it is a major hindrance to the accurate determination by existing systems of continuous EF/EDV since an accurate estimate of τ is required.

One other shortcoming of the frequency-domain techniques described above that use the lagged normal model is that they calculate estimates based on only a limited number of harmonics. Consequently, faster time constants, which lie outside the bandwidth of the primary (first ten) PRBS harmonics, are poorly determined.

What is needed is therefore a system that can produce continuous estimates of the EF or EDV, or both, but whose estimates are substantially unaffected by low frequency-induced errors in the dc and τ estimates; this in turn would provide more accurate CO and EF/EDV measurements, respectively. This invention provides such a system, and a corresponding method, for determining CO and EF/EDV.

SUMMARY OF THE INVENTION

The invention provides a method for estimating a cardiac performance value, such as cardiac output CO and/or cardiac ejection fraction EF of a patient according to which an indicator (preferably heat) is injected at an upstream position in a patient's heart according to a predetermined injected indicator signal x(t). An indicator concentration sensor such as a thermistor then senses a local indicator concentration signal y(t) at a downstream position. The region from and including the upstream position to and including the downstream position forms a channel for the blood.

The indicator concentration signal is then divided into at least one sub-signal that is synchronous with the injected indicator signal. A processing system then calculates a first time-domain, channel relaxation model that has each sub-signal as an input. It then also calculates a decay parameter τ as a pre-determined function of the first, time-domain channel relaxation model. The processor then estimates the cardiac performance value as a predetermined function of the decay parameter τ.

In the preferred embodiments of the invention, the injected indicator signal x(t) is generated as a series of alternating transitions between a high state and a low state. Examples of suitable injected indicator signals includes a periodic, pseudo-random binary sequence (the preferred embodiment), trains of random or periodic random square waves, and even non-binary signals such as trigonometric functions and spread spectrum signals.

According to one aspect of the invention referred to as y_tau integration, for each transition of the injected indicator signal, a corresponding segment of the indicator concentration signal is isolated, with each segment comprising one of the sub-signals. For each segment of the indicator concentration signal, a segment relaxation parameter is then calculated. The processor then calculates the decay parameter τ as a predetermined function of the segment relaxation parameters.

In implementations of the invention in which the injected indicator signal is periodic, with a plurality of transitions during each period, each sub-signal of the indicator concentration signal corresponds to one period of the injected indicator signal. The y_tau integration embodiment of the invention, further preferably includes sign-rectification of all the segments before the decay parameter τ is calculated.

In y_tau integration, the step of calculating the decay parameter τ preferably includes the sub-steps of generating the first time-domain, channel relaxation model as a time-domain exponential function of the decay parameter; calculating a cost function that is a predetermined function of the sum of differences between the exponential function of the decay parameter and the respective segments of the indicator concentration signal; and calculating the decay parameter τ by determining a minimum of the cost function.

In embodiments of the invention in which CO is to be estimated, the system according to the invention includes a heart rate monitor. The cost function is then preferably a predetermined function of both the decay parameter τ and a steady-state channel gain parameter (dc). The processing system according to the invention then determines optimum values of the decay parameter τ and the steady-state channel gain parameter dc that minimize the cost function. It then calculates the cardiac output (CO) value as a predetermined function of the optimum value of the steady-state channel gain parameter, and calculates the cardiac ejection fraction (EF) as a predetermined function of the optimum value of the steady-state channel gain parameter and the measured heart rate (HR).

According to a second aspect of the invention referred to as y_avg integration, the processor divides the indicator concentration signal y(t) into a plurality of the sub-signals such that each sub-signal corresponds to one period of the injected indicator signal. An average of the sub-signals is then calculated to form an averaged indicator concentration signal. The channel relaxation model is thereby generated as a time-domain, lagged-normal function of both the decay parameter τ and the steady-state channel gain parameter (dc). A cost function is then evaluated that is a predetermined function of the difference between the averaged indicator concentration signal and the time-domain, lagged-normal function convolved with the injected indicator signal. The system then determines optimum values of the decay parameter τ and the steady-state channel gain parameter dc that minimize the cost function. Values for CO and EF are then calculated as predetermined functions of the optimum values of the steady-state channel gain parameter (for CO) and the steady-state channel gain parameter and the measured heart rate (for EF).

In another embodiment of the invention that includes combined parameter estimation, estimates of the decay parameter τ and of the steady-state gain dc are determined in three different ways: using y_tau integration, y_avg integration, and by determining the optimum values to minimize a cost function based on a frequency-domain lagged normal model of the channel. The three different estimates are then normalized and combined using a weighted average.

BRIEF DESCRIPTION OF THE DRAWINGS

FIGS. 2A–2D illustrate the method according to the invention for generating and evaluating multiple relaxation waveforms to obtain a composite relaxation waveform.

DETAILED DESCRIPTION

Two main embodiments of the invention are described below. In broadest terms, the pseudo-random nature of a preferred indicator injection signal, x(t), is exploited in the time domain to extract accurate estimates of the dc gain (from which cardiac output CO can be calculated) and of the indicator relaxation time constant τ from which EF/EDV can be calculated given a relatively easily determined heart rate HR. This is achieved using integration, that is, a cumulative combination, of a sensed indicator signal y(t), synchronized with the injected indicator signal x(t). In the preferred embodiments of the invention, the input signal x(t) signal is pseudo-random, which provides pseudo-random noise cancellation. Low-frequency noise that, in systems according to the prior art, is coupled with the input signal, is effectively de-coupled. The two main complimentary methods for synchronous signal integration are described separately below.

Before delving into these methods, however, the main hardware components of the invention are defined and described. Hardware components that are specific to the particular embodiments of the invention are defined along with the other particularities of the respective embodiments.

General System Components

Figure 1:
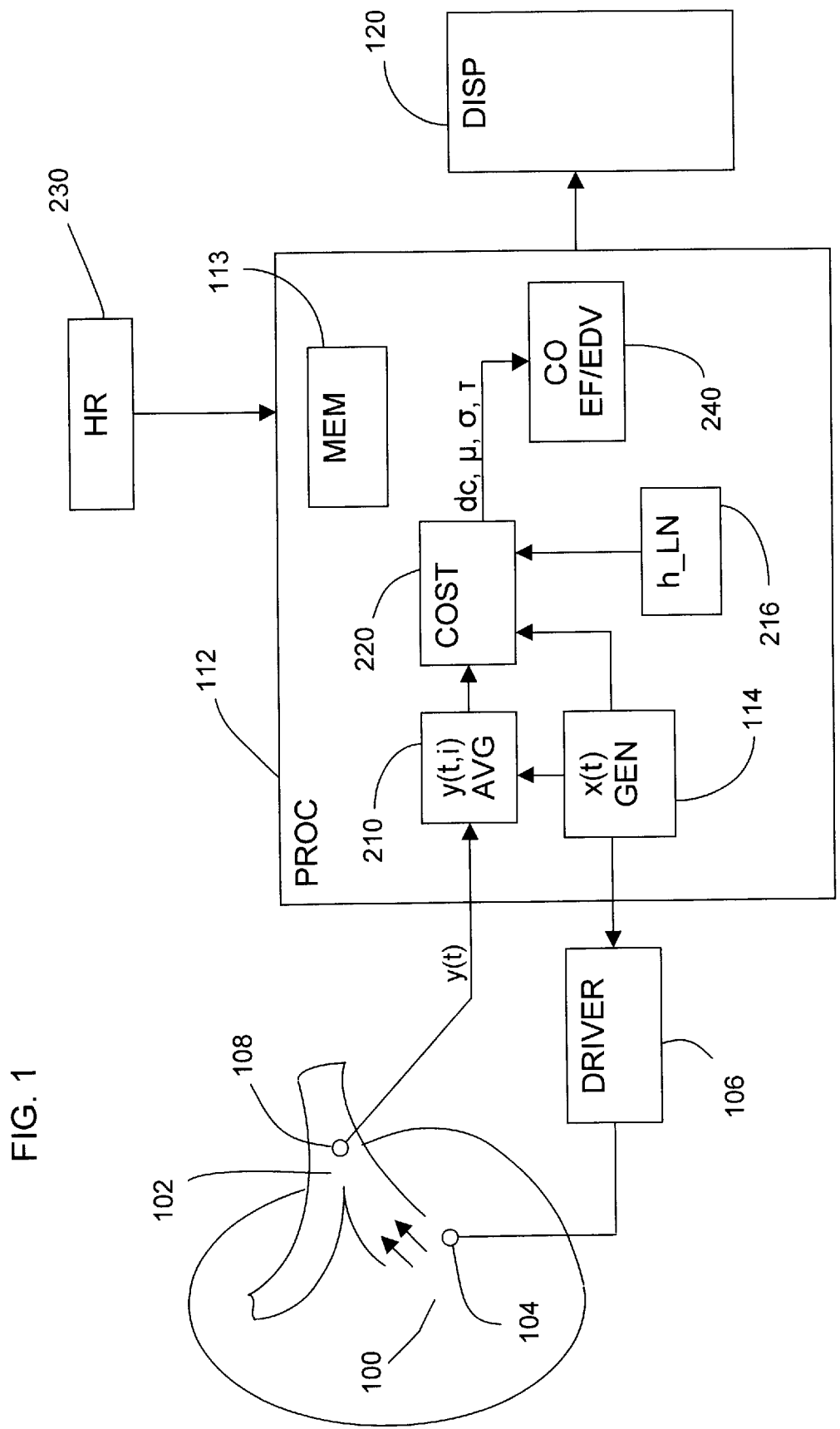
FIG. 1 is a block diagram of a first embodiment of a system according to the invention for continuous estimation of the cardiac output, as well as of the ejection fraction, or end diastolic volume, or both, of a patient's heart.
Figure 3:
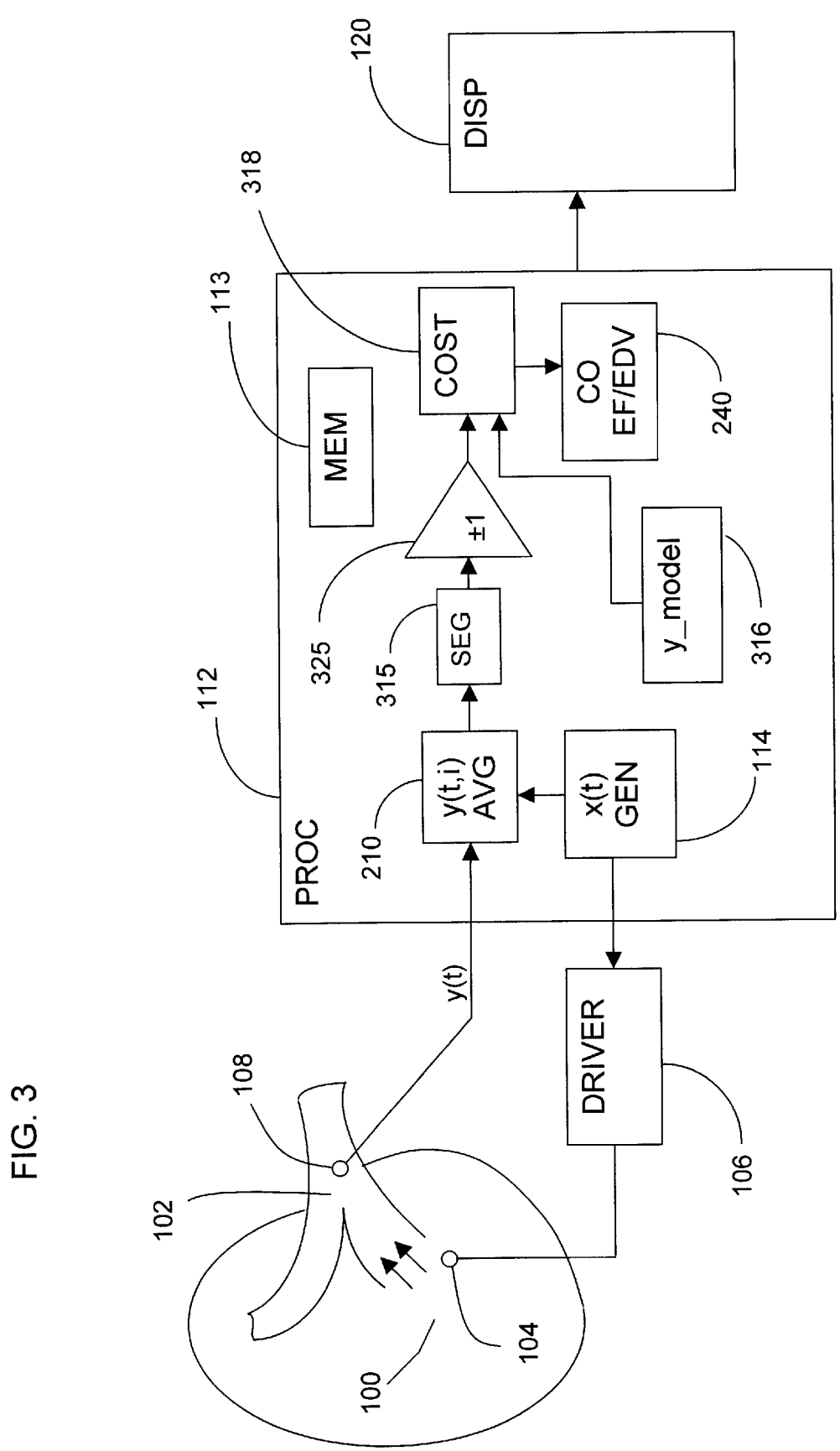
FIG. 3 is a block diagram of a second embodiment of the invention.

FIG. 1 is a block diagram of a first embodiment of a system according to the invention for continuous estimation of the ejection fraction (EF), or end diastolic volume (EDV), or both, of a patient's heart; this system also generates an estimate of the cardiac output (CO). FIG. 1 also shows, however, the system components used in both main embodiments of the invention. For accurate measurement of the cardiac output CO of a patient, it is advantageous to inject an indicator into the blood in or near the patient's right atrium/ventricle 100 and to sense an indicator concentration signal in or proximal to the branch of the pulmonary artery 102. These injection and sensing positions are therefore assumed below in order to illustrate the preferred embodiments of the invention. The flow of blood from the right atrium/ventricle and through the pulmonary artery is indicated in FIG. 1 by the parallel arrows.

In order to increase accuracy, it is preferable to use a heat signal as the basis of a measurement of CO. As is explained below, however, this is only one possible indicator that may be used. An indicator injection device 104 is positioned in the right atrium 100. In the preferred embodiment in which the indicator is heat, the injection device is an electrical heating element 104. The heating element 104 is preferably an electrically resistive element whose temperature is determined by the current or voltage supplied to the element via a driving circuit 106, which is drives the heating element 104 so that its temperature follows a predetermined signal profile.

An indicator concentration sensor 108 is positioned at the downstream position in the pulmonary artery 102. In the preferred embodiment in which the indicator is heat, the sensor is a thermistor or some similar temperature-sensing element 108. The heating element 104 and the thermistor 108 are preferably mounted spaced apart at or near the distal end of a catheter, which is then fed into a vein of the patient and threaded into and through the vein until the heating element and the thermistor reach their operating positions. This technique is well known and is therefore not described further.

Conventional power and clock devices are preferably included to supply electrical power and timing signals to the driving circuit 106 and the other components of the invention. These devices are neither illustrated nor described further since they are well known.

It is assumed here that the thermistor 108 has a fast response, meaning that its instantaneous temperature signal y(t) closely and predictably reflects the actual instantaneous temperature of the blood whose temperature it is measuring. If this assumption is not valid, then an "inverse" transfer function step may be included in subsequent filtering to compensate for the effects of the slow response time of the sensor. This optional procedure is outlined below.

The electrical output signal from the thermistor 108, which determines the indicator concentration signal y(t), is applied as an input signal to a main processing system (processor) 112. The processor 112 may be implemented using any known architecture. For example, the processing system 112 may include a single dedicated microprocessor, along with standard auxiliary components such as memory 113 and conditioning circuitry on a dedicated board. On the other hand, the processing system 112 used in this invention may also share its resources with other unrelated systems, such as other instruments for patient monitoring. The various sub-processing components of the processor 112 are described below for the different embodiments of the invention. Any or all of these components may be implemented in either hardware or software, as those skilled in the art will understand.

One sub-processing component common to all embodiments of the invention is an injection signal generator 114. This sub-processor (implemented, as the general processing system 112 itself, in either software or hardware), generates the pattern of ON-OFF states that the heating element 104 is to follow.

The processor 112 is also connected to or includes a conventional display (and/or printing) unit 120, by means of which the calculated CO and the EF and/or EDV values are displayed to the user. The display 120 includes any conventional display driver or other standard circuitry.

Injected Indicator Signal x(t)

In the preferred embodiments of the invention, the injected indicator signal (preferably, heat) profile x(t) that the injection device follows is as described in the McKown '733 patent. In this system, as in the Yelderman system also mentioned above, the heat signal is generated based on a pseudo-random binary sequence (PRBS) in order to provide an efficiently detectable concentration signal y(t) (preferably temperature) at the downstream sensing position, with a high spectral content yet with low and therefore trauma-reducing average applied heat. Moreover, although the signal is pseudo-random, it is still at all times known to the system, so that the characteristics of the calculations based on it are well understood and well conditioned.

The mathematical structure and other properties of a PRBS are well known. In general, a PRBS will consist of $2^n-1$ binary states, with the total number of "ON" or "1" states being one more or less than the number of "OFF" or "0" states, and with the states distributed pseudo-randomly. In the described embodiments of the invention, a 15-state PRBS (n=4) is assumed over a period of 30–60 seconds. This length matches the bandwidth of the heart's physiological washout characteristics. Other PRBS lengths may be used in the invention, however, and modifications to the equations below necessary to adjust them to the different PRBS sequence will be obvious to those skilled in the art. The best PRBS length for a given application can be chosen using normal experimental methods.

In the following description of the various embodiments of the invention, it is assumed that heat is used as the indicator that is injected into the blood. As such, the upstream indicator driver is a heating element and the downstream indicator sensor is a thermistor. This is the preferred choice because this technology is well-established and was the choice in a prototype and tests of the invention. Using the method described in McKown '733, moreover, using heat as an indicator gives highly accurate CO estimates. Nonetheless, heat is but one possible indicator that may be used in this invention. As long as the indicator injector and sensor used generate measurable and sufficiently well-defined and non-noisy signals (which can be determined by normal experimentation), then the signals may be used in this invention with no or only easily realizable modifications to the rest of the system.

As one example of a different indicator that may be used in this invention, known luminescent materials may be injected into the patients heart instead, using known devices. Luminescence may then be sensed downstream, also using known sensors, and the variation in luminescence may serve as an indicator concentration signal. Weakly radioactive dyes or agents may be used similarly.

It is also possible to inject fluids so as to follow a similar injection pattern. As long as the injection period is slow enough, small boluses may, for example, be released into the blood stream so as to approximate a PRBS profile, and the concentration of the bolus material may be sensed downstream using corresponding known sensors to establish an indicator concentration signal. In sum, as long as the indicator injector and sensor used generate measurable and sufficiently well-defined and non-noisy signals (which can be determined by normal experimentation), then the signals may be used in this invention with no or only easily realizable modifications to the rest of the system.

y_avg Integration

The first embodiment of the invention generates accurate estimates of the dc and $\tau$ parameters wholly in the time domain by averaging a plurality of cycles of the measured output signal y(t) synchronously with x(t). The averaging process, which operates as a form of signal integration, improves accuracy and helps eliminate the effects of low-frequency noise. The averaged output signal is then preferably used in a cost function that includes a time-domain version of the lagged normal model of the channel. These steps will now be described in greater detail, with reference to both FIG. 1 and FIGS. 2A–2B.

FIG. 2A illustrates one period of the 15-state PRBS input signal x(t) used in the preferred embodiments of the invention. A "1" or "ON" state indicates that the heating element 104 should be at its maximum allowable power. A "0" or "OFF" state indicates that the power to the heating element should be turned off. Note that adjacent (in time) states in a PRBS are sometimes the same. Thus, states 4–7 are all "ON", and states 8–10 are all "OFF".

In one prototype of the invention, the PRBS states could be varied from 2–4 seconds, giving a total time of 30–60 seconds for one complete period of x(t), and thus for one cycle of y(t). This time range proved to give reliable, stable readings over the several periods used in the preferred embodiments of the invention.

FIG. 2B illustrates a typical thermistor signal y(t) corresponding to the sensed temperature of the blood in response to the input signal of FIG. 2A under the assumption of little or no thermal noise. As one would expect, there is a bit of a lag in the response (corresponding to the parameter $\mu$ in the lagged normal model) at each transition, estimated, however, using an optimization routine such as the one described below.

One complication encountered when estimating the lagged normal shape parameters based on y(t) is that a single measurement of y(t) may be overly affected by low-frequency noise such as that caused by natural or mechanical ventilation. In the preferred embodiment of the invention, several cycles of y(t) are preferably sensed and recorded by the processing system 112 and then these are averaged. Note that each output signal y(t,i) will be derived from the same input signal x(t) profile, which is transmitted through the same channel, and which is preferably periodic. Each period of x(t) therefore gives a period of y(t); in other words, y(t) is parsed into y(t,i), each triggered on x(t). Let y(t,i) be the i'th of N sensed output signals y(t), corresponding to the response to the i'th input cycle x(t,i) of x(t). Assuming that each y(t,i) is viewed from the same starting point, that is, the same x(t,i) start time, which are independent of i, then all the values of y(t,i) would ideally coincide if there were no noise and all properties of the blood channel remained constant.

To reduce the effects of noise, several y(t,i) values are therefore preferably measured, recorded, and then arithmetically averaged, to form a single, integrated output signal yavg(t), which is used in subsequent calculations. Thus:

$$yavg(t)=1/N*SUM\ y(t,i) \qquad \text{(Equation 8)}$$

where the sum is taken over i=1 to N.

The necessary accumulation of y(t,i) measurements, and the averaging step, are carried out, for example, in a output-averaging sub-processing block (processing module) or routine 210. The injection signal generator 114 is preferable connected to (either using hardware triggering or simply by software) this output-averaging block 210 to provide triggering and thus a consistent definition of the starting and finishing times for each y(t,i) measurement.

Because the ventilation noise is not pseudo-random, whereas x(t) (and thus, the response of y(t)) is, ventilation noise will be reduced by this averaging (integration) process, depending on how many y(t,i) runs are averaged. Clinical trials have indicated that excellent suppression of the ventilation noise can be achieved for n=7. The more output signals are averaged, however, the longer it will take to get CO, EF and EDV estimates, and the more likely it will be that the system will not detect short-term changes in these values. The "best" value for n will therefore depend of the patient and the application, and can be chosen using normal clinical and experimental methods.

Once the value yavg has been determined, it is used, in this first embodiment of the invention, in a cost function that includes the lagged normal model, but here, expressed in the time-domain as the lagged normal model $h_{LN}$ whose parameters may be stored in a model sub-processing block or routine module 216. The general structure of the lagged normal model is well known; one time-domain form of the lagged normal model that has proven in clinical tests to give accurate results for dc and $\tau$ is defined as follows:

$$h\_{LN}(t|dc,\mu,\sigma,\tau)=dc*1/(2\tau)*\exp\{-(t-\mu)/\tau+\tfrac{1}{2}*(\sigma/\tau)^2\}*\{\text{erf}[(t-\mu-\sigma^2/\tau)/(\sigma\text{SQRT2})]+\text{erf}[(\mu+\sigma^2/\tau)/(\sigma\text{SQRT2})]\}/fs \quad \text{(Equation 9)}$$

where:

erf is the standard error function;

SQRT indicates the square root;

fs is the frequency with which y(t) is sampled, for example, by the y(t,i) averaging block 210 or whichever conventional conditioning and sampling circuitry in or connected to the processing system 112 is included to receive, condition and sample the thermistor 108 output signal y(t).

The steady-state temperatures determine the dc-gain, whereas the shape of the relaxation curve is determined by the lagged normal shape parameters ($\mu$, $\sigma$, $\tau$).

In this embodiment of the invention, the yavg(t) waveform is then analyzed by a cost-calculating sub-processing block or routine 220 with the aid of this time-domain, lagged normal model impulse response $h\_{LN}$ by finding, using any known optimization algorithm, the state vector X=(dc, $\mu$, $\sigma$, $\tau$) that minimizes the following cost function:

$$\text{Cost\_yavg}=\int[\text{yavg}(t)-\text{ymodel\_avg}(t)]^2 dt \quad \text{(Equation 10)}$$

Where:

ymodel_avg=x(t) convolved with $h\_{LN}(X)$; and the functions yavg(t) and ymodel_avg(t) are differenced point-by-point, that is, sample by sample.

This optimization then provides estimates of the desired parameters dc and $\tau$, as well as of $\mu$ and $\sigma$.

As is known, for example from McKown '733, the system can estimate EF as long as it also has estimates of $\tau$ and the heart rate HR. The optimization routine just described gives $\tau$; HR is preferably supplied by any conventional monitoring system 230 that is connected to the processing system 212. A cardiac performance sub-processing block or processing module 240 therefore then determines EF by calculating the expression EF=1−exp(−60/($\tau\cdot$HR)).

Observe further that CO=HR·SV, where SV is the stroke volume and CO is measured in units of volume (liters) per minute. This simply expresses that the amount of blood the heart pumps out in a minute is equal to the amount it pumps out on every beat (stroke) times the number of beats (strokes) per minute. Finally, note that the end diastolic volume (EDV) and the ejection fraction (EF) are related as follows:

EF=SV/EDV, which also expresses the intuitive relationship that the pumping efficiency (EF) of the heart is the ratio between how much blood the heart pumps out on every beat (contraction) and how much blood is in the heart chamber just before the beat. Rearranging this expression, one sees that EDV=SV/EF.

The cardiac performance sub-processing system 240 also calculates CO based on the value dc received from optimization routine and the known, predetermined conversion constant K, since CO=K/dc. Dividing CO by the heart rate HR (obtained from the heart rate monitor 230, the sub-processing system 240 then calculates SV=CO/HR, and once SV is known, the sub-processing system 220 can then calculate EDV as SV/EF, having already estimated EF by calculating 1−exp(−60/($\tau\cdot$HR)). The invention may of course be used to calculate not only CO and/or EF/EDV, but any other cardiac performance parameter that are known functions of CO and/or EF/EDV.

The sub-processing systems 216, 240 need not be separate units. Rather, they may both be implemented as a single processing device. Indeed, they may also be implemented simply as different software modules of the processor 212.

Thermistor Defiltering

As is mentioned above, in some implementations of the invention, the response of the sensor (for example, thermistor) 108 may not be fast enough to justify the assumption that its instantaneous indicator (for example, temperature) concentration signal y(t) closely and predictably reflects the actual instantaneous indicator concentration (temperature) in the blood. To compensate for this, according to the invention, the transfer function (equivalently: step response) of the sensor 108 (here, thermistor) is pre-calculated and the "inverse" of this transfer function is applied to Hxy so as to "de-filter" or compensate for the effects of the slow response time of the sensor. There are several known ways to characterize the step response of a transfer function, the easiest of which is simply to apply a series of impulse input signals to it, to measure each response, and then to average the results. The parameters of the transfer function can then be stored in the processor 112 either in the existing memory 113, or in a separate permanent memory device such as an EEPROM that would be associated with the individual sensor.

y_tau Integration

In a second embodiment of the invention, rising and falling segments of the output signal y(t), corresponding to the ON-OFF states of the injected input signal x(t), are isolated, and then a cost function of these rising and falling segments of y(t) is minimized to provide estimates of dc and $\tau$. This embodiment will now be described with reference to FIGS. 2A–D and FIG. 3.

In a 15-state PRBS, there are eight transitions, either from "ON" to "OFF" (negative-going) or vice versa (positive-going). These transitions are labeled in parentheses in FIG. 2A: Transitions (1), (3), (5) and (7) are positive, and transitions (2), (4), (6) and (8) are negative. The indicator concentration signal will display a mainly exponential decay profile at each ON-OFF transition; for each OFF-ON transition, it will display an exponential rise profile. Because the perturbations to the medium are small, the channel can in these applications be assumed to form a linear, time-invariant system, the time constant at every transition, whether decay or rise, will be the same, namely the parameter $\tau$. Each transition thus provides a basis for a determination of $\tau$ since each transition marks a separate relaxation. Low-frequency noise will be canceled out, since it will in general extend over several states and will thus pass several "ON-OFF boundaries." High-frequency noise will be canceled due to both the pseudo-random nature of the PRBS, the segmentation, and the accompanying integration (see below).

As in the y_avg embodiment described above, several (n) cycles of the thermistor output signal y(t) are preferably accumulated and averaged to form the output signal y*(t) that is used in the optimization calculations described below. Thus, y*(t)=1/n*SUM y(t,i), for i=1, . . . , n as before.

Note that n may be equal to one, that is, the averaging step may be omitted altogether for this embodiment, that is, the invention is able, however, to generate estimates of REF and CO using y_tau integration (described below) from the output signal corresponding to a single cycle of the input signal. This allows the system to generate accurate values of dc and $\tau$ without having to wait for several PRBS periods.

Now consider FIGS. 2A–2C once again. For each transition in x(t), there will be a corresponding local maximum (for negative transitions) or minimum (for positive transitions) in each y(t,i), and thus in y*(t). Each transition thus marks one endpoint of a new relaxation segment for y*(t). These points of transition of y(t) can be determined in several known ways, but the easiest is simply for the processing system 112, for example, in a segment separation sub-processing block 315 or routine, to scan the accumulated measured data points of y*(t) to identify local minima and maxima, and to designate as separate segments the data points located between each of the consecutive pairs of minima/maxima.

Immediately after negative transitions, the corresponding segment of y*(t) will display a decay profile; immediately after positive transitions, y*(t) will display a rise profile. Because the system is assumed to be linear and time-invariant, the parameter of rise (+τ) will simply be the negative to the parameter of decay (−τ). Multiplying each rising segment by −1, for example, in a sign-rectification sub-processing block or routine 214, will thus convert it into a "decaying" segment, with the same time constant τ. Segments (1), (3), (5), and (7), which are numbered according to the number of their beginning transition, are thus preferably "inverted" by multiplication by −1, in a sign-rectification sub-processing block or routine 325. (Of course, one could equivalently turn all the segments into "rising" segments by multiplying by −1 all the decaying segments. Alternatively, one need not sign-rectify the segments at all, although this will increase the "bookkeeping" needed to ensure the correct sign for each individual segment in the cost-function models described below. All such sign adjustments in the modeling expressions discussed below will be obvious, albeit tedious and error-prone, for those skilled in the art.)

FIG. 2C illustrates the eight segments of y*(t) of FIG. 2B separated, aligned in time, and sign-rectified so that they all display decay profiles. Let y*(t,m) be the m'th segment of y*(t). Note that segments (1), (2), (5) and (8) correspond to single state durations, segments (6) and (7) each represent the response to two-state periods of x(t), and segments (4) and (3) represent, respectively, three-state and four-state periods of the PRBS input signal x(t), as can be seen in FIG. 2A.

Because of the segment separation process, in which only a portion of each actual output measurement between transitions is included, each segment may represent a different measurement time period or range. Thus, each segment y*(t,m) will extend from an initial time $t_0$ (which can be set to zero for all segments) to a time $t_m$. These time periods, if not known to be the same for all segments, must then be stored for each segment, for example, in the memory 113, or in the segment separation subprocessing block 315.

The relaxation profile of the segments of y*(t) may be modeled in different ways. The parameters and functions for the chosen model may, as before, be stored in a sub-processing block or routine 316. For example, each relaxation segment can be modeled as a scaled, lagged-normal step response:

$$y_{MODEL\_TAU}(t)=A^*\{1-[EXP1^*(ERF1-ERF2)+ERF3]\}$$

where:

EXP1=$\exp((\mu-t)/\tau+0.5^*(\sigma/\tau)^2)$
ERF1=$\text{erf}((\mu-t)/\sqrt{2}^*\sigma)+\sigma/(\sqrt{2}^*\tau))$
ERF2=$\text{erf}(\mu/(\sqrt{2}^*\sigma)+\sigma/(\sqrt{2}^*\tau))$
ERF3=$\text{erf}((t-\mu)/(\sqrt{2}^*\sigma))$
  exp is the standard exponential function;
  erf is the standard error function; and
  SQRT indicates the square root.

In practice, however, in order to ensure that the data for each segment truly represents points on the decay/rise portions of the segments, it is preferable to select as a y*(t) data segment only the portion of each "curve" away from the peak and trough. This can be done in several ways, and is a well-known technique in the area of signal processing. For example, the system may isolate the portion of each rise/decay segment between 80% of the peak value and 30% above the minimum value, or between 80% and 30% of the peak. Alternatively, the segments may be selected as time slices between the maxima and minima, for example, the central 50% portion in time between each adjacent peak and trough. These percentages or times may, of course, be selected differently using normal experimental methods and design considerations to ensure that the portion of y*(t) used in the following calculations represents a portion of the true relaxation curve away from transition effects and low-level noise.

In this second embodiment of the invention, the preferred model is a simple exponential, that is, the channel is modeled according to the following general relaxation expression:

$$y_{MODEL\_TAU}(t)=A^*\exp(-t/\tau) \quad \text{(Equation 11)}$$

where A is a starting or base-line amplitude and τ is the decay parameter. Note that, after the sign-rectification step, all segments will display a decay response, with the same underlying decay parameter τ.

FIG. 2D illustrates a single decay curve formed as a composite of the eight decay curves (segments) y*(t,1) . . . y*(t,8) shown in FIG. 2C. All eight segments last at least one state; four segments ((3), (4), (6), and (7)) last for at least two states; two segments ((3) and (4)) last for three states; and only one segment (3) lasts four states. Each segment represents, however, a valid measurement of the decay during the states over which it extends. There are thus eight one-state long measurements of the decay parameter τ, four two-state long measurements, two three-state measurements, and one four-state measurement.

One way to generate a composite τ measurement would therefore be to average the portions of the segments (or line segments formed from the logarithm of the curve segments) during each state period. This would provide four τ estimates: one estimate for the average of the eight segment portions in the first state period, one estimate for the average of the four segment portions ((3), (4), (6), and (7)) lying in the second state period (from the end of the first to the beginning of the second), one estimate for the average of the two segment portions ((3) and (4)) lying in the third state period (from the end of the second to the beginning of the third), and one estimate based on the portion of y*(t,3) that lies in the fourth state period. These four τ estimates can then be normalized to account for their different durations and averaged to provided a composite estimate of τ.

In this embodiment, the parameters dc and τ are preferably determined by finding the minimum of the cost function that is the sum of the squares of the integral (point-by-point sum) of differences between each segment y*(t,m) and the corresponding $y_{MODEL\_TAU}(t)$ taken over the time interval $t_0$ to $t_m$. In one implementation of the invention, the cost function with $y_{MODEL\_TAU}(t)$ for each segment, that was minimized, using a standard optimization algorithm in a cost evaluation sub-processing block or routine 318, was:

$$\text{Cost\_}y_{TAU}=\Sigma\int[y^*(t,m)+dc\cdot k-A_m\cdot\exp(-t/\tau)]^2 dt \quad \text{(Equation 12)}$$

where the summation is over all the values of m, the integration (in this case, numerical, or point-by-point addition and subtraction) is taken over the time interval $[t_0, t_m]$ for segment m, and:

k is an experimentally predetermined power constant to provide a zero-mean expected value. In one implementation of the invention, k was equal to maximum input PRBS power divided by 2, multiplied by a predetermined flow constant (in liters per minute), multiplied by either (1−⅛₅), for ON states of the input signal or (1+⅟₁₅) for OFF states of the input signal (since there were 8 ON but only 7 OFF states of the 15 total states). The (dc·k) term thus accounts for off-set and flow as a function of power and flow; and $A_m$ is the amplitude of the exponential for each segment. The other parameters are as defined earlier.

In this cost function, dc, $\tau$ and $A_m$ are unknowns. The amplitude values, $A_m$, are, however, irrelevant to the calculations of CO or EF/EDV and can be ignored. Alternatively, the various $y^*(t,m)$ curves can all be pre-scaled to the same amplitude value A; it will, however, in general be easier simply to let these values "float," let the optimization routine determine $A_m$, and simply ignore the results—this has been shown experimentally to provide better estimates of dc and $\tau$. The minimization will therefore provide estimates for dc and $\tau$, from which CO and ED/EDV can be calculated by the sub-processing block 220 as before.

Because each relaxation segment $y^*(t,m)$ is exponential, one other way to view the identification routine for dc and $\tau$ is to consider the logarithm of $y^*(t,m)$. Taking the logarithm of these curves produces line segments. The slope of the segments are all the decay parameter $\tau$. The "y intercepts," (values for $t_0$) are different, however, since the starting amplitudes for different segments depend on how long it has been since the last transition. In FIG. 2B, for example, at transition (3), the blood has not yet had time to cool down to the base-line temperature before the next positive transition starts. The various segments will thus be parallel, but not necessarily coincident, line segments in log space. An equivalent, logarithmic cost function can then be used instead of the one described above; the slopes of the log $y^*(t,m)$, which may, for example, be averaged, will the provide a value for $\tau$.

One advantage of the y_tau embodiment of the invention is that it folds the noisy signal y(t) down on itself in a manner that tends both to whiten and reduce the noise. This is especially true in the first two state durations (with eight and four segments, irespectively), where the relaxation has the greatest curvature.

In both of the embodiments of the invention described above—y_avg and y_tau estimation—the output signal y(t) is divided or "parsed" into sections or "sub-signals," each synchronous with state changes in the input signal x(t). In the case of the y_avg estimation method, the sub-signals are the entire y(t,i) output signals. In the case of y_tau estimation method, the output signal is also divided into sub-signals corresponding to periods of the input signal, but each sub-signal is then further parsed into segments with boundaries corresponding to the individual state changes (0 to 1, or 1 to 0) of the input signal.

Although the sections are synchronous with the input signal x(t), they are not synchronous with any particular noise source. Moreover, it is not necessary to synchronize the injected indicator signal x(t) with the patient's heart itself, for example, with particular R-wave events. The indicator concentration signal y(t) will therefore in general also not be synchronous with the heart cycle, This synchronization with the injected indicator signal, but not necessarily with the heart, reduces the effect of the noise in the calculations of dc and $\tau$.

Combined Parameter Estimation

Figure 4:
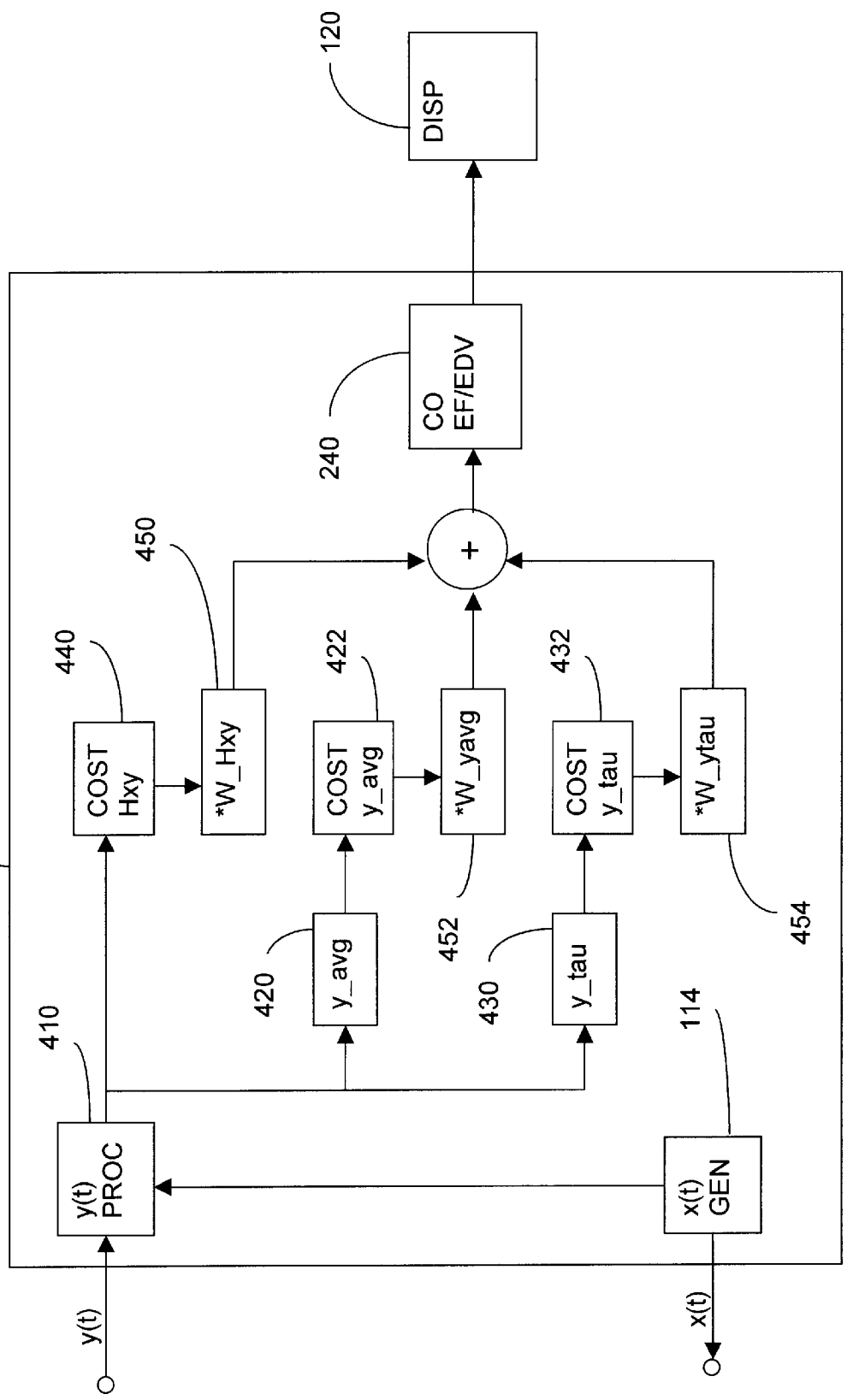
FIG. 4 is a block diagram of a combined estimation embodiment of the invention.

In yet another embodiment of the invention, which is illustrated in FIG. 4, the dc, $\tau$ parameter estimation is obtained by using known numerical optimization techniques to minimize a cost function defined by a combination of the frequency-based lagged normal modeling technique described in McKown '733 and either or, preferably, both of the y_avg and y_tau integration techniques described below.

In FIG. 4, most of components of the invention that are not relevant to describe this embodiment have been omitted for clarity, but should be assumed to be present and as described above. As FIG. 4 illustrates, a common input signal conditioning circuit 410 is included to handle such conventional processing steps as sampling and analog to digital conversion, as needed. The yavg and ytau integration steps, including cost determination, are performed in respective sub-processing blocks or routines 420, 422, and 430, 432, respectively. The parameters of the frequency-domain lagged normal model, along with the processing routine necessary for computing its cost function, are included in the sub-processing block 440. Sub-processing blocks (or memory positions) with weights for the three different estimation sub-routines used in this embodiment of the invention are shown as blocks 450, 452, 454. These components and their function are described below.

In this embodiment, a combined cost function is defined as follows:

$$\text{Cost\_total} = \text{Cost\_Hxy}^*\text{W\_Hxy}/\text{df\_Hxy} + \text{Cost\_yavg}^*\text{W\_yavg}/\text{df\_yavg} + \text{Cost\_ytau}^*\text{W\_ytau}/\text{df\_ytau} \quad \text{(Equation 13)}$$

where

Cost_Hxy is defined below, and corresponds to Equation 5.

Cost_yavg is defined as in Equation 10.

Cost_ytau is defined as in Equation 12.

W_Hxy, W_yavg, and W_ytau are predetermined, fixed or variable cost weights.

df_Hxy, df_yavg, and df_ytau are normalization terms that are defined below.

The Cost_Hxy cost function is preferably defined as:

$$\text{Cost\_Hxy}(X) = \text{Power}^*\text{SUM}(n)\{(\text{Hxy}(\omega_n) - \text{Hxy}_{LN}(\omega_n|X))^2 * W(\omega_n)\}/\text{df\_Hxy} \quad \text{(Equation 14)}$$

where:

$\text{Hxy}(\omega_n)$ is the measured frequency domain transfer function relating y(t) to x(t) at the n'th harmonic of the PRBS x(t) input signal;

$\text{Hxy}_{LN}(\omega_n)$ is the frequency domain transfer function model, preferably the lagged normal model according to Equation 4; and $W(\omega_n)$ is a weight measuring the input signal to output noise power ratio at $\omega_n$ as in Equation 5.

The factor Power is the heater power in watts during the ON states of x(t)—this makes Cost_Hxy have units of temperature (degrees C) squared error, which is the same as in Cost_yavg and Cost_ytau. The df_Hxy normalization accounts for the degrees of freedom. Making the usual statistical assumptions of orthogonality:

$$\text{df\_Hxy} = \text{Nfreq} - \text{Nstate} - 1 \quad \text{(Equation 15)}$$

where:

Nfreq is the number of harmonics ($\omega_n$ for n=1 to Nfreq); here Nfreq=10; and Nstate is the number of parameters being estimated, here N state=4 for the four parameter lagged normal state vector X=[dc, $\mu$, $\sigma$, $\tau$], which provides df_Hxy=5.

The df_yavg normalization term similarly accounts for the degrees of freedom, for example:

df_yavg=SPR−Nstate−1

Where, SPR (Samples Per Run) is the number of samples in yavg. Using a typical sampling rate of Fs=10 Hz and a PRBS cycle of 1 minute, SPR=600, so that df_yavg=595.

The Cost_ytau as used in the preferred embodiment requires the inclusion of individual amplitude normalization parameters, $A_m$, for each of the eight data segments. If the system were allowed to reach steady state before a state change, these amplitudes would all equal unity. In general, however, this is not the case, so the segments must be normalized to the same amplitude to begin their decays. Several empirical and/or analytic methods for this normalization can be used (e.g. ratiometric). However, in the preferred embodiment, the normalization is determined by the optimization/fitting routine itself, as described above.

If SPS is the number of samples per state, and assuming that segments are "clipped" at 80% of peak values, as described above, then the number of samples N_ytau in y*(t,m) is equal to:

SPS−n80 for m=1,2,3, 6;

2*SPS−n80 for m=7, 8;

3*SPS−n80 for m=5; and

4*SPS−n80 for m=4.

Where n80 is the number of samples before the 80% level for each respective segment. Here, it is assumed (also for the purposes of illustration), that there is no "clipping" of data segments below any specific level.

The df_ytau normalization term also accounts for the degrees of freedom. For example, df_ytau=4*(SPS−n80)+2*(2*SPS−n80)+3*SPS−n80+ 4*SPS−n80−10−1.

Typically SPS=40 and n80=10, which provides df_ytau= 509.

Note that both Cost_Hxy and Cost_yavg depend on the data and the lagged normal state vector X=[dc, $\mu$, $\sigma$, $\tau$] whereas the Cost_ytau depends on the data and X_ytau= [dc, $\tau$, $A_1$, ... $A_8$]. The selection of the weights W_Hxy, W_yavg, and W_ytau define various embodiments of the invention. For example, setting any one or two of the weights to zero removes the respective models from the calculations. In one prototype of the invention, setting all the weights equal to ⅓ has been shown to give adequate performance. For the sake of normalization, however, the weights should preferably always sum to 1.

Although the 'x(t) signal synchronous integration of y(t)' according to the invention minimizes the effects of most low frequency noise, it has been experimentally observed that, about 10% of the time, the mechanical ventilator is set to a high harmonic of the PRBS, which makes it synchronous with the PRBS itself and reduces the benefit of the invention. Adjusting the state duration such that the noise is no longer synchronous is one possible solution. It is preferred, however, to include a notch filter in the signal conditioning circuitry for y(t), as is found in the McKown '414 and '733 systems. Such a notch filter will minimize the residual effects of synchronous ventilator noise.

Defining normalized power spectral density measurements of x(t) and y(t) as PSDx(f)=PSD(x(t))/sum(PSD(x(t)) and PSDy(f)=PSD(y(t))/sum(PSD(y(t)) then a conventional FFT-based notch filter can be implemented using known techniques, which nulls the FFT(y) bins where PSDy(f)−PSDx(f)>Null−Threshold provided the frequency f is in the range of expected mechanical ventilator settings, say 11 breaths per minute. Furthermore, if the PRBS cycle time is set at 60 seconds, the first 10 harmonics of the measured Hxy will be below 0.1666 Hz, which is below the lowest expected ventilator setting of 11 breaths per minute or 0.183 Hz. This ensures that the ventilator will not affect Hxy data; it also has the side benefit of always updating the CO/EF/EDV estimation once per minute.

Alternative, pure time-domain combined parameter estimation

In the combined or composite cost function defined in Equation 13, two time-domain and one frequency-domain cost functions are weighted, normalized and summed to create a total cost function from which estimates of the decay parameter $\tau$ and the steady-state channel gain parameter (dc) are obtained. It would also be possible to combine any two of these cost functions—instead of all three—to obtain estimates of $\tau$ and dc that in most cases will be more accurate than if only one cost function is used, In particular $\tau$ and dc could be estimated wholly in the time domain by forming the total cost function as the weighted, normalized, sum of the two time-domain cost functions, that is:

Cost_total=Cost_avg*W_yavg/df_yavg+Cost_ytau*W_ytau/ df_ytau

The needed changes to the weights and normalization factors can be determined using normal experimental and theoretical techniques known to those skilled in the art.

Alternative Injected Input Signals

In all of the preferred embodiments of the invention, the injected input signal is in the form of a pseudo-random binary sequence (PRBS). This has the advantages described above, for example, high spectral content with low average applied heat, but a PRBS input sequence is not necessary to cause the relaxation phenomenon from which dc and $\tau$ are calculated. Similarly, it is preferable to have the input signal be periodic, since this allows for proper synchronization of different measured values for y(t) and meaningful averaging in those embodiments of the invention that include averaging of the different measurements of y(t). With suitable adjustments, which will be obvious to those skilled in the art, any pattern of ON-OFF signals that lead to relaxation may be used, as long as the beginning and end points of any sequence are properly defined. Examples of alternative input signals include a simple square wave and a random train of ON-OFF states.

It would even be possible to use input signals that are other than two-state (ON-OFF), such as those with a trigonometric profile (such as a sine wave) or a spread-spectrum signal such as a "chirp" input. Additional, known processing blocks or signal conditioning circuitry will then normally be required to compensate for the effect of such a signal on the channel's transfer function.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

We claim:

1. A method for estimating a cardiac performance value of a patient comprising the following steps:

injecting an indicator at an upstream position in a heart according to a predetermined injected indicator signal x(t);

sensing with an indicator concentration sensor a local indicator concentration signal y(t) at a downstream position, the region from and including the upstream position to and including the downstream position forming a channel for the blood;

dividing the indicator concentration signal into at least one sub-signal synchronous with the injected indicator signal;

calculating a first time-domain, channel relaxation model having each sub-signal as an input;

calculating a decay parameter τ as a pre-determined function of the first, time-domain channel relaxation model; and estimating the cardiac performance value as a predetermined function of the decay parameter τ.

2. A method as in claim 1, further comprising the following steps:

generating the injected indicator signal x(t) as a series of alternating transitions between a high state and a low state;

for each transition of the injected indicator signal, isolating a corresponding segment of the indicator concentration signal, each segment comprising one of the sub-signals;

for each segment of the indicator concentration signal, calculating a segment relaxation parameter; and calculating the decay parameter τ as a predetermined function of the segment relaxation parameters.

3. A method as in claim 2, in which:

the injected indicator signal is periodic, with a plurality of transitions during each period; and each sub-signal of the indicator concentration signal corresponds to one period of the injected indicator signal.

4. A method as in claim 3, in which the injected indicator signal is generated as a pseudo-random binary sequence.

5. A method as in claim 2, further including the step of sign-rectifying all the segments before calculating the decay parameter τ.

6. A method as in claim 2, in which the step of calculating the decay parameter τ includes the following sub-steps:

generating the first time-domain, channel relaxation model as a time-domain exponential function of the decay parameter;

calculating a cost function that is a predetermined function of the sum of differences between the exponential function of the decay parameter and the respective segments of the indicator concentration signal; and calculating the decay parameter τ by determining a minimum of the cost function.

7. A method as in claim 6, in which the cardiac performance value of the patient is the cardiac ejection fraction.

8. A method as in claim 6, further including the step of measuring the patient's heart rate (HR).

9. A method as in claim 8, further including the following steps:

generating the cost function as a predetermined function of both the decay parameter τ and a steady-state channel gain parameter (dc);

determining optimum values of the decay parameter τ and the steady-state channel gain parameter dc that minimize the cost function;

calculating a cardiac output (CO) value as a predetermined function of the optimum value of the steady-state channel gain parameter; and calculating a cardiac ejection fraction (EF) as a predetermined function of the optimum value of the steady-state channel gain parameter and the measured heart rate (HR).

10. A method as in claim 1, further comprising the following steps:

generating the injected indicator signal x(t) as a series of alternating transitions between a high state and a low state;

for each transition of the injected indicator signal, isolating a corresponding segment of the indicator concentration signal, each segment comprising one of the sub-signals;

for each segment of the indicator concentration signal, calculating a segment relaxation parameter; and calculating the decay parameter τ as a predetermined function of the segment relaxation parameters;

in which:

the injected indicator signal is periodic, with a plurality of transitions during each period;

each sub-signal of the indicator concentration signal corresponds to one period of the injected indicator signal;

the step of calculating the decay parameter τ includes the following sub-steps:

generating the channel relaxation model as a time-domain exponential function of the decay parameter;

calculating a cost function that is a predetermined function of the sum of differences between the exponential function of the decay parameter and the respective segments of the indicator concentration signal; and calculating the decay parameter τ by determining a minimum of the cost function.

11. A method as in claim 10, further including the following steps:

measuring the patient's heart rate (HR);

generating the cost function as a predetermined function of both the decay parameter τ and a steady-state channel gain parameter (dc);

determining optimum values of the decay parameter τ and the steady-state channel gain parameter dc that minimize the cost function;

calculating a cardiac output (CO) value as a predetermined function of the optimum value of the steady-state channel gain parameter; and calculating a cardiac ejection fraction (EF) as a predetermined function of the optimum value of the decay parameters and the measured heart rate (HR).

12. A method as in claim 1, further comprising the following steps:

generating the injected indicator signal x(t) as a periodic signal with a plurality of alternating transitions between a high state and a low state during each period;

dividing the indicator concentration signal y(t) into a plurality of the sub-signals such that each sub-signal corresponds to one period of the injected indicator signal;

calculating an average of the sub-signals to form an averaged indicator concentration signal;

generating the channel relaxation model as a time-domain, lagged-normal function of both the decay parameter τ and a steady-state channel gain parameter (dc);

calculating a cost function that is a predetermined function of the difference between the averaged indicator concentration signal and the time-domain, lagged-normal function convolved with the injected indicator signal;

determining optimum values of the decay parameter τ and the steady-state channel gain parameter dc that minimize the cost function;

calculating a cardiac output (CO) value as a predetermined function of the optimum value of the steady-state channel gain parameter; and calculating a cardiac ejection fraction (EF) as a predetermined function of the optimum value of the decay parameter τ and the measured heart rate (HR).

13. A method as in claim 12, in which the injected indicator signal is generated as a pseudo-random binary sequence.

14. A method as in claim 1, in which:

A) the injected indicator signal x(t) is generated as a periodic input signal having, during each period, a plurality of alternating transitions between a high state and a low state, each sub-signal of the indicator concentration signal corresponding to one period of the injected indicator signal;

B) the time-domain, channel relaxation model is a first channel model; further including the following steps:

C) evaluating the first channel model for each sub-signal according to the following sub-steps:
  i) for each transition of the injected indicator signal, isolating a corresponding time-domain segment of the indicator concentration signal;
  ii) for each segment of the indicator concentration signal, calculating a segment relaxation parameter;
  iii) generating the first channel model as a time-domain exponential function of the decay parameter;
  iv) calculating a first cost function that is a predetermined function of the sum of differences between the exponential function of the decay parameter and the respective segments of the indicator concentration signal; and
  v) calculating a first estimate of the decay parameter τ by determining a minimum of the first cost function;

D) evaluating a second time-domain channel model according to the following sub-steps:
  i) calculating an average of a plurality of the sub-signals to form an averaged indicator concentration signal;
  ii) generating the second channel model as a time-domain, lagged-normal function of both the decay parameter τ and a steady-state channel gain parameter (dc);
  iii) calculating a second cost function that is a predetermined function of the difference between the averaged indicator concentration signal and the time-domain, lagged-normal function convolved with the injected indicator signal;
  iv) determining second optimum values of the decay parameter τ and the steady-state channel gain parameter dc that minimize the second cost function;

E) evaluating a third, n-harmonic, frequency-domain channel model according to the following sub-steps:
  i) measuring an averaged transfer function of the channel;
  ii) calculating an error measure between the averaged transfer function and a frequency-domain, lagged normal model of the channel;
  iii) calculating a third cost function as a predetermined function of the error measure for each of the n harmonics;
  iv) determining third optimum values of the decay parameter τ and the steady-state channel gain parameter dc that minimize the third cost function;

F) calculating a total cost function as the weighted, normalized sum of the first, second and third cost functions;

G) determining composite optimum values of the decay parameter τ and the steady-state channel gain parameter dc that minimize the total cost function;

H) measuring the patient's heart rate (HR);

I) calculating a cardiac output (CO) value as a predetermined function of the composite optimum value of the steady-state channel gain parameter dc; and J) calculating a cardiac ejection fraction (EF) as a predetermined function of the composite optimum value of the steady-state channel gain parameter dc, of the composite optimum decay parameter τ, and of the measured heart rate (HR).

15. A system for estimating a cardiac performance value of a patient comprising:

an input signal generator generating a predetermined injected indicator signal x(t);

signal injection means for injecting an indicator at an upstream position in a heart according to the injected indicator signal x(t);

an indicator concentration sensor sensing a local indicator concentration signal y(t) at a downstream position, the region from and including the upstream position to and including the downstream position forming a channel for the blood;

processing means provided for:
  dividing the indicator concentration signal into at least one sub-signal y(t,i) synchronous with the injected indicator signal x(t);
  calculating a first time-domain, channel relaxation model having each sub-signal as an input;
  calculating a decay parameter τ as a pre-determined function of the first, time-domain channel relaxation model; and
  estimating the cardiac performance value as a predetermined function of the decay parameter τ.

16. A system as in claim 15, in which:

the input signal generator is further provided for generating the injected indicator signal x(t) as a series of alternating transitions between a high state and a low state; and a segment separation sub-processing module is included in the processing means for isolating, for each transition of the injected indicator signal x(t), a corresponding segment of the indicator concentration signal, each segment comprising one of the sub-signals;

a cost-calculation sub-processing module forming means for each segment of the indicator concentration signal, calculating a segment relaxation parameter; and a cardiac performance sub-processing module forming means for calculating the decay parameter τ as a predetermined function of the segment relaxation parameters.

17. A system as in claim 16, in which the cost-calculation sub-processing module further forms means:

for generating the first time-domain, channel relaxation model as a time-domain exponential function of the decay parameter;

for calculating a cost function that is a predetermined function of the sum of differences between the exponential function of the decay parameter and the respective segments of the indicator concentration signal; and for calculating the decay parameter τ by determining a minimum of the cost function.

18. A system as in claim 17, further including:
a heart rate monitor connected to the processing means, measuring the patient's heart rate (HR);
in which:
the cardiac performance value of the patient is the cardiac ejection fraction;
the cost function is a predetermined function of both the decay parameter τ and a steady-state channel gain parameter (dc);
the cost-calculation sub-processing module is further provided for determining optimum values of the decay parameter τ and the steady-state channel gain parameter dc that minimize the cost function;
the cardiac performance sub-processing module is further provided:
for calculating a cardiac output (CO) value as a predetermined function of the optimum value of the steady-state channel gain parameter; and
for calculating a cardiac ejection fraction (EF) as a predetermined function of the optimum value of the decay parameter τ and the measured heart rate (HR).

19. A method for estimating a cardiac performance value of a patient comprising the following steps:
injecting an indicator at an upstream position relative to a heart according to a predetermined injected indicator signal x(t);
sensing with an indicator concentration sensor a local indicator concentration signal y(t) at a downstream position, the region from and including the upstream position to and including the downstream position forming a channel for the blood;
dividing the indicator concentration signal into at least one sub-signal synchronous with the injected indicator signal;
calculating a first time-domain, channel relaxation model having each sub-signal as an input;
calculating one or more model parameters as a predetermined function of the first, time-domain channel relaxation model; and
estimating the cardiac performance value as a predetermined function of the one or more parameters.

20. A method as in claim 19, wherein the one or more model parameters calculated is a steady-state channel gain parameter (dc).

21. A method as in claim 20 wherein the cardiac performance value of the patient is cardiac output (CO).

22. A method as in claim 19, wherein the one or more model parameters calculated is the decay parameter τ.

23. A method as in claim 22, wherein the cardiac performance value of the patient is the cardiac ejection fraction.

24. A method as in claim 19, wherein the one or more model parameters are estimated by averaging a plurality of cycles of the local indicator concentration signal y(t) synchronously with the injected indicator signal x(t).

25. A method as in claim 24, wherein the averaged output signal is used in a cost function that is minimized to provide an estimate of the one or more model parameters.

26. A method as in claim 25, wherein the cost function includes a time-domain version of the lagged normal model of the channel.

27. A method as in claim 25, wherein the cost function is generated from rising and falling segments of the output signal y(t).

28. A method as in claim 19, further comprising the following steps:
generating the injected indicator signal x(t) as a series of alternating transitions between a high state and a low state;
for each transition of the injected indicator signal, isolating a corresponding segment of the indicator concentration signal, each segment comprising one of the sub-signals; and
for each segment of the indicator concentration signal, calculating a steady state channel gain parameter (dc);
in which:
the injected indicator signal is periodic, with a plurality of transitions during each period;
each sub-signal of the indicator concentration signal corresponds to one period of the injected indicator signal;
the step of calculating the steady state channel gain parameter (dc) includes the following sub-steps:
generating the channel relaxation model as a time-domain exponential function of the steady state channel gain parameter (dc);
calculating a cost function that is a predetermined function of the sum of differences between the exponential function of the steady state channel gain parameter (dc) and the respective segments of the indicator concentration signal; and
calculating the steady state channel gain parameter (dc) by determining a minimum of the cost function.

29. A method for estimating a cardiac performance value of a patient comprising the following steps:
injecting an indicator at an upstream position in a heart according to a predetermined injected indicator signal x(t) as a periodic signal with a plurality of alternating transitions between a high state and a low state during each period;
sensing with an indicator concentration sensor a local indicator concentration signal y(t) at a downstream position, the region from and including the upstream position to and including the downstream position forming a channel for the blood;
dividing the indicator concentration signal into a plurality of sub-signals synchronous with the injected indicator signal such that each sub-signal corresponds to one period of the injected indicator signal;
calculating an average of the sub-signals to form an averaged indicator concentration signal;
calculating a first time-domain, channel relaxation model having each sub-signal as an input as a time-domain, lagged-normal function of a steady-state channel gain parameter (dc);
calculating a cost function that is a predetermined function of the difference between the averaged indicator concentration signal and the time-domain, lagged-normal function convolved with the injected indicator signal;
determining optimum values of the steady-state channel gain parameter dc that minimize the cost function; and
calculating a cardiac output (CO) value as a predetermined function of the optimum value of the steady-state channel gain parameter.

30. A system for estimating a cardiac performance value of a patient comprising:
an input signal generator generating a predetermined injected indicator signal x(t);
signal injection means for injecting an indicator at an upstream position in a heart according to the injected indicator signal x(t);
an indicator concentration sensor sensing a local indicator concentration signal y(t) at a downstream position, the region from and including the upstream position to and including the downstream position forming a channel for the blood;
processing means provided for:
dividing the indicator concentration signal into at least one sub-signal y(t,i) synchronous with the injected indicator signal x(t);
calculating a first time-domain, channel relaxation model having each sub-signal as a input;
calculating one or more model parameters as a predetermined function of the first, time-domain channel relaxation model; and
estimating the cardiac performance value as a predetermined function of the one or more model parameters.

31. A system as in claim 30, in which:
the input signal generator is further provided for generating the injected indicator signal x(t) as a series of alternating transitions between a high state and a low state; and
a segment separation sub-processing module is included in the processing means for isolating, for each transition of the injected indicator signal x(t), a corresponding segment of the indicator concentration signal, each segment comprising one of the sub-signals;
a cost-calculation sub-processing module forming means for calculating a cost calculation parameter for each segment of the indicator concentration signal; and
a cardiac performance sub-processing module forming means for calculating the one or more model parameters as a predetermined function of the segment relaxation parameters.

32. A system as in claim 31, in which the cost-calculation sub-processing module further forms means:
for generating the first time-domain, channel relaxation model as a time-domain exponential function of the one or more model parameters;
for calculating a cost function that is a predetermined function of the sum of differences between the exponential function of the one or more model parameters and the respective segments of the indicator concentration signal; and
for calculating the one or more model parameters by determining a minimum of the cost function.

33. A system as in claim 32, further including:
a heart rate monitor connected to the processing means, measuring the patient's heart rate (HR);
in which:
the cardiac performance value of the patient is the cardiac ejection fraction;
the cost function is a predetermined function of both the decay parameter $\tau$ and a steady-state channel gain parameter (dc);
the cost-calculation sub-processing module is further provided for determining optimum values of the decay parameter $\tau$ and the steady-state channel gain parameter dc that minimizes the cost function;
the cardiac performance sub-processing module is further provided:
for calculating a cardiac output (CO) value as a predetermined function of the optimum value of the steady-state channel gain parameter; and
for calculating a cardiac ejection fraction (EF) as a predetermined function of the optimum value of the decay parameter $\tau$ and the measured heart rate (HR).

34. A system as in claim 30, wherein the one or more model parameters calculated is a steady-state channel gain parameter (dc).

35. A system as in claim 34 wherein the cardiac performance value of the patient is cardiac output (CO).

36. A system as in claim 30, wherein the one or more model parameters calculated is the decay parameter $\tau$.

37. A system as in claim 36, wherein the cardiac performance value of the patient is the cardiac ejection fraction.

* * * * *